US010765298B2

(12) United States Patent
Ozaki

(10) Patent No.: US 10,765,298 B2
(45) Date of Patent: Sep. 8, 2020

(54) PROCESSOR, MANAGEMENT APPARATUS, AND MEDICAL SYSTEM

(71) Applicant: OLYMPUS CORPORATION, Hachioji-shi, Tokyo (JP)

(72) Inventor: Takashi Ozaki, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 145 days.

(21) Appl. No.: 16/173,365

(22) Filed: Oct. 29, 2018

(65) Prior Publication Data

US 2019/0059697 A1 Feb. 28, 2019

Related U.S. Application Data

(63) Continuation of application No. PCT/JP2017/012515, filed on Mar. 28, 2017.

(30) Foreign Application Priority Data

Aug. 29, 2016 (JP) .................................. 2016-167127

(51) Int. Cl.
*A61B 1/00* (2006.01)
*G16H 30/20* (2018.01)
(Continued)

(52) U.S. Cl.
CPC ............ *A61B 1/00009* (2013.01); *A61B 1/04* (2013.01); *A61B 5/0035* (2013.01); *G16H 10/40* (2018.01);
(Continued)

(58) Field of Classification Search
CPC .. G06F 16/9535; G06F 16/248; G06F 3/0482; G06F 16/951; G06F 16/9566;
(Continued)

(56) References Cited

U.S. PATENT DOCUMENTS

2004/0136025 A1* 7/2004 Moriyama ........... G03G 15/556
358/1.14
2010/0115469 A1* 5/2010 Shigemori ............ G06F 19/321
715/838
(Continued)

FOREIGN PATENT DOCUMENTS

JP 2002-171376 A 6/2002
JP 2008-036353 A 2/2008
(Continued)

OTHER PUBLICATIONS

Jun. 20, 2017 Search Report issued in International Application No. PCT/JP2017/012515.
(Continued)

*Primary Examiner* — Neal Sereboff
(74) *Attorney, Agent, or Firm* — Oliff PLC

(57) ABSTRACT

A processor includes: a generation unit that generates first-performed-examination identification information in correlation with reserved-examination identification information and generates second-performed-examination identification information in correlation with the reserved-examination identification information, the first-performed-examination identification information being for identifying a first performed examination, the second-performed-examination identification information being for identifying a second performed examination; a recording medium that records a first-performed-examination result accompanied by the first performed-examination identification information and a second-performed-examination result accompanied by the second performed-examination identification information; and a memory that records first count information and second count information, the first count information being related to the number of pieces of data obtained in the first performed examination and associated with the first-performed-examination identification information, the second
(Continued)

count information being related to the number of pieces of data obtained in the second performed examination and associated with the second-performed-examination identification information.

9 Claims, 12 Drawing Sheets

(51) Int. Cl.
  *A61B 5/00* (2006.01)
  *G16H 10/60* (2018.01)
  *G16H 10/40* (2018.01)
  *G16H 30/40* (2018.01)
  *G16H 40/60* (2018.01)
  *A61B 1/04* (2006.01)

(52) U.S. Cl.
  CPC ............ *G16H 10/60* (2018.01); *G16H 30/20* (2018.01); *G16H 30/40* (2018.01); *G16H 40/60* (2018.01); *A61B 5/72* (2013.01)

(58) Field of Classification Search
  CPC .. G06F 16/9577; G06F 16/958; G06F 16/972; G06F 19/3418; G06F 3/04815; G06F 3/04847; G06F 3/0488; G06F 3/04883; G06F 40/186; G06F 19/32; G06F 19/321; G06F 19/34; G06F 3/1211; G06F 3/1239; G06F 3/1292; G06F 16/2457; G06F 16/29; G06F 16/41; G06F 16/538; G06F 16/54; G06F 16/5866; G06F 19/3456; G06F 3/002; G06F 8/20; G06F 8/60; G06F 8/77; G06Q 20/047; G06Q 20/0655; G06Q 20/3224; G06Q 20/3276; G06Q 30/0601; G06Q 10/0633; G06Q 10/087; G06Q 10/10; G06Q 10/1095; G06Q 30/02; G06Q 30/06; G06Q 30/0633; G06Q 50/10; G06Q 50/22; G06Q 50/24
  See application file for complete search history.

(56) References Cited

U.S. PATENT DOCUMENTS

| | | | |
|---|---|---|---|
| 2011/0190595 A1* | 8/2011 | Bennett | A61B 5/6846 600/301 |
| 2012/0041785 A1 | 2/2012 | Tsunomori et al. | |
| 2012/0134410 A1 | 5/2012 | Kawasaki et al. | |
| 2013/0215246 A1 | 8/2013 | Ozaki | |
| 2015/0031954 A1* | 1/2015 | Kimoto | A61B 1/00006 600/118 |

FOREIGN PATENT DOCUMENTS

| | | |
|---|---|---|
| JP | 2010-099159 A | 5/2010 |
| JP | 2010-152624 A | 7/2010 |
| JP | 2010-288186 A | 12/2010 |
| JP | 2012/0043095 A | 3/2012 |
| JP | 2013-066242 A | 4/2013 |
| JP | 2016-085505 A | 5/2016 |
| WO | 2010/113615 A1 | 10/2010 |
| WO | 2012/0043095 A1 | 4/2012 |

OTHER PUBLICATIONS

Jun. 20, 2017 Written Opinion of the International Searching Authority issued in Patent Application No. PCT/JP2017/012515.
May 29, 2018 Decision to Grant a Patent issued in Japanese Patent Application No. 2018-500807.
Mar. 6, 2018 Office Action issued in Japanese Patent Application No. 2018-500807.

* cited by examiner

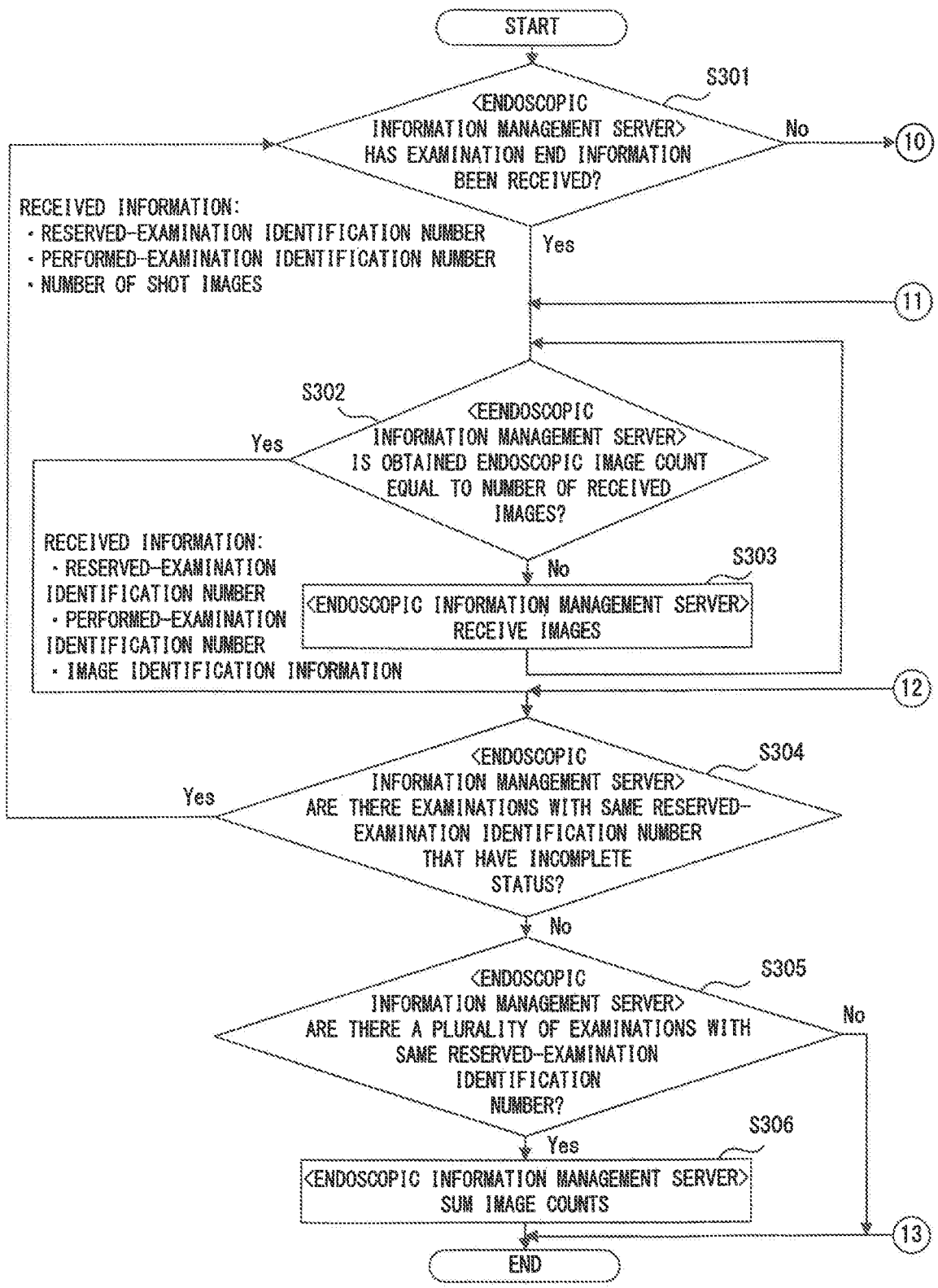
F I G. 9A

PROCESSOR, MANAGEMENT APPARATUS, AND MEDICAL SYSTEM

CROSS-REFERENCE TO RELATED APPLICATIONS

This application is based upon and claims the benefit of priority of the prior Japanese Patent Application No. 2016-167127, filed Aug. 29, 2016, the entire contents of which are incorporated herein by reference.

This is a Continuation Application of PCT Application No. PCT/JP2017/012515, filed Mar. 28, 2017, which was not published under PCT Article 21(2) in English.

FIELD

The present invention relates to a processor that obtains examination data, a management apparatus that manages information on an examination, and a medical system that includes the processor and the management apparatus.

BACKGROUND

As an example of the medical systems conventionally used in the medical field, a medical system is known in which endoscopic images shot by a video system center during an endoscopic examination are managed by an endoscopic information management system. The video system center is an endoscope processor to which a scope (endoscope) is connected. The endoscope processor may be referred to as an endoscopic video processor or an endoscopic video-image signal processing apparatus.

In the medical system, when an examination based on a reserved examination preset by the endoscopic information management system is performed, endoscopic images shot by the video system center during the examination are transferred to the endoscopic information management system. When the transfer is finished, information related to the examination (including information on the number of endoscopic images shot in the examination) is cleared out (deleted) in the video system center. This is because the storage medium of the video system center has only a limited storage capacity to store information related to examinations.

A medical image management system that includes a plurality of image storage apparatuses is also known as another example of the medical systems used in the medical field (see Japanese Laid-open Patent Publication No. 2010-152624). In this system, when a control unit has received examination order information from a HIS/RIS via a communication unit, it is determined on the basis of an image storage status DB of a storage unit whether a medical image obtained in a past examination of a subject patient correlated with the received examination order information is stored in any of a plurality of NASs, and when it is determined that the received information is stored in any of the NASs, an NAS that has stored therein the medical image obtained in a past examination of the subject patient is chosen in advance as a storage location for medical images to be generated using a modality on the basis of the received examination order information. This allows a storage location for medical images to be chosen efficiently while enabling medical images, including images obtained in a past examination of the same patient, to be accessed efficiently at diagnosis.

SUMMARY

A first aspect of the invention provides a medical system that includes a processor and a management apparatus, wherein the processor includes: an input unit to which reserved-examination identification information for identifying a preset reserved examination is input from the management apparatus; a performed-examination identification information generation unit that generates first-performed-examination identification information in correlation with the reserved-examination identification information and generates second-performed-examination identification information in correlation with the reserved-examination identification information, the first-performed-examination identification information being for identifying a first performed examination performed in response to the reserved-examination identification information being input to the input unit, the second-performed-examination identification information being for identifying a second performed examination performed in response to the same reserved-examination identification information as the reserved-examination identification information being input to the input unit; a recording medium that records a first-performed-examination result and a second-performed-examination result, the first-performed-examination result being data obtained in the first performed examination and accompanied by the first performed-examination identification information, the second-performed-examination result being data obtained in the second performed examination and accompanied by the second performed-examination identification information; and a memory that records first count information and second count information, the first count information being related to the number of pieces of data obtained in the first performed examination and associated with the first-performed-examination identification information, the second count information being related to the number of pieces of data obtained in the second performed examination and associated with the second-performed-examination identification information, the management apparatus includes: a recording apparatus that records the first performed-examination result accompanied by the first-performed-examination identification information and the second performed-examination result accompanied by the second-performed-examination identification information, the first and second performed-examination results being transmitted from the recording medium of the processor; and a calculation unit that calculates the total number of pieces of data of the first and second performed-examination results recorded in the recording apparatus that are accompanied by pieces of performed-examination identification information generated in correlation with the same reserved-examination identification information, and when the sum of the numbers indicated by the first and second count information transmitted from the memory of the processor that have been associated with pieces of performed-examination identification information generated in correlation with the same reserved-examination identification information is not equal to the total number of pieces of data calculated by the calculation unit, the management apparatus receives data that has not been recorded in the recording apparatus of the management apparatus among the data recorded in the recording medium of the processor.

Another aspect of the invention provides a processor that includes: an input unit to which reserved-examination identification information for identifying a preset reserved examination is input from an external management apparatus; a performed-examination identification information generation unit that generates first-performed-examination identification information in correlation with the reserved-examination identification information and generates second-performed-examination identification information in correlation with the reserved-examination identification information, the first-performed-examination identification information being for identifying a first performed examination performed in response to the reserved-examination identification information being input to the input unit, the second-performed-examination identification information being for identifying a second performed examination performed in response to the same reserved-examination identification information as the reserved-examination identification information being input to the input unit; a recording medium that records a first-performed-examination result and a second-performed-examination result, the first-performed-examination result being data obtained in the first performed examination and accompanied by the first performed-examination identification information, the second-performed-examination result being data obtained in the second performed examination and accompanied by the second performed-examination identification information; and a memory that records first count information and second count information, the first count information being related to the number of pieces of data obtained in the first performed examination and associated with the first-performed-examination identification information, the second count information being related to the number of pieces of data obtained in the second performed examination and associated with the second-performed-examination identification information, wherein when the total number of pieces of data of the first and second performed-examination results transmitted from the recording medium, recorded in a recording apparatus within the external management apparatus, and accompanied by pieces of performed-examination identification information generated in correlation with the same reserved-examination identification information is not equal to the sum of the numbers indicated by the first and second count information transmitted from the memory to the external management apparatus and associated with pieces of performed-examination identification information generated in correlation with the same reserved-examination identification information, the processor transmits data that has not been recorded in the recording apparatus of the external management apparatus, among the data recorded in the recording medium.

Still another aspect of the invention provides a management apparatus that includes: a recording apparatus that records first and second performed-examination results transmitted from an external processor, the first performed-examination result being data obtained in a first performed examination performed in response to reserved-examination identification information being input to the external processor, the first performed-examination result being accompanied by first-performed-examination identification information generated in correlation with the reserved-examination identification information so as to identify the first performed examination, the second performed-examination result being data obtained in a second performed examination performed in response to the same reserved-examination identification information as the reserved-examination identification information being input to the external processor, the second performed-examination result being accompanied by second-performed-examination identification information generated in correlation with the reserved-examination identification information so as to identify the second performed examination; and a calculation unit that calculates the total number of pieces of data of the first and second performed-examination results recorded by the recording apparatus and accompanied by pieces of performed-examination identification information generated in correlation with the same reserved-examination identification information, wherein the management apparatus receives first count information and second count information from the external processor, the first count information being related to the number of pieces of data obtained in the first performed examination and associated with the first-performed-examination identification information, the second count information being related to the number of pieces of data obtained in the second performed examination and associated with the second-performed-examination identification information, and when the sum of the numbers indicated by the first and second count information associated with pieces of performed-examination identification information generated in correlation with the same reserved-examination identification information is not equal to the total number of pieces of data calculated by the calculation unit, the management apparatus receives, from the external processor, data that has not been recorded in the recording apparatus.

BRIEF DESCRIPTION OF DRAWINGS

FIG. 9A is a flowchart illustrating an exemplary process further performed as an endoscopic examination process performed by a medical system (example 1)

DESCRIPTION OF EMBODIMENTS

Figure 1:
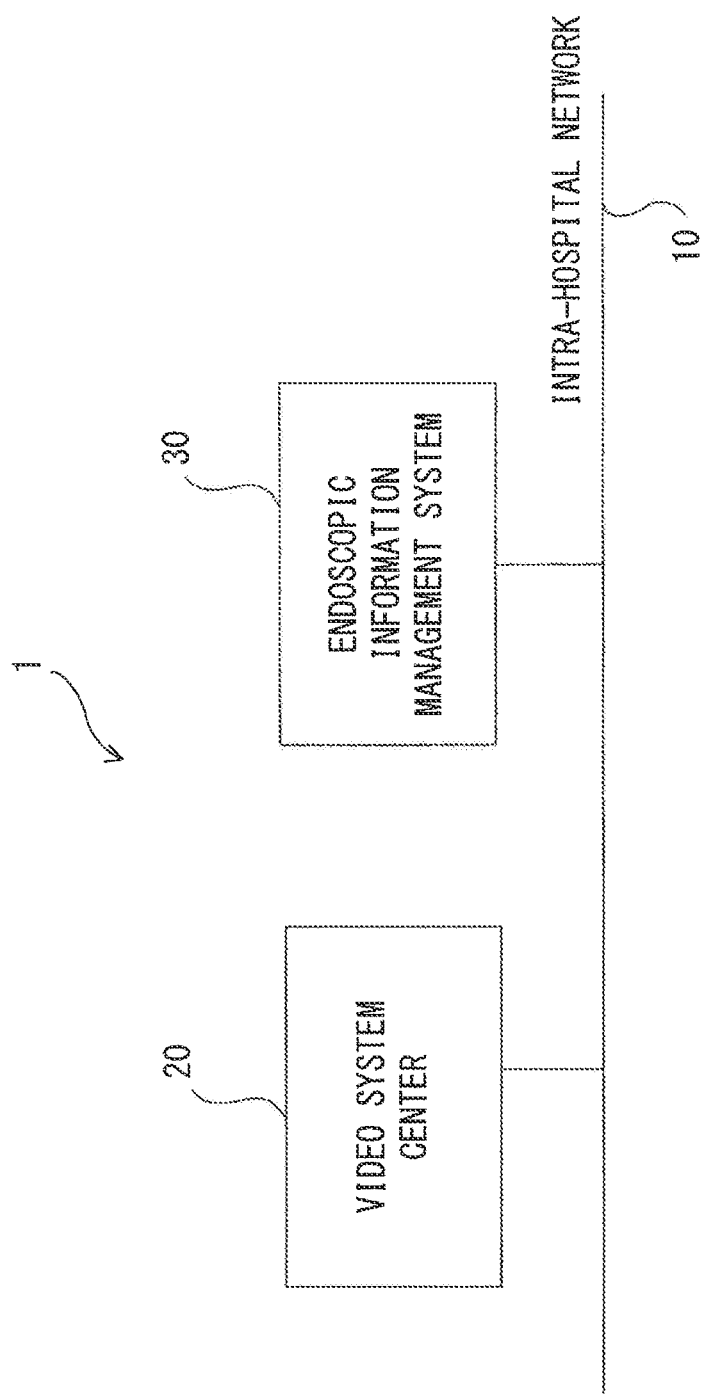
FIG. 1 illustrates an exemplary configuration of a medical system in accordance with an embodiment.

The following describes embodiments of the present invention by referring to the drawings.

FIG. 1 illustrates an exemplary configuration of a medical system in accordance with an embodiment of the invention.

In FIG. 1, a medical system 1 is provided within a hospital and includes an intra-hospital network 10, a video system center 20, and an endoscopic information management system 30, wherein the video system center 20 and the endoscopic information management system 30 are connected to the intra-hospital network 10. The video system center 20 and the endoscopic information management system 30 are capable of communicating with each other over the intra-hospital network 10.

The intra-hospital network 10 is, for example, a local area network (LAN). The video system center 20 is provided within an endoscopic examination room and obtains endoscopic examination data (e.g., endoscopic images). The endoscopic information management system 30 manages information related to an endoscopic examination (including information transmitted from the video system center 20).

Figure 2:
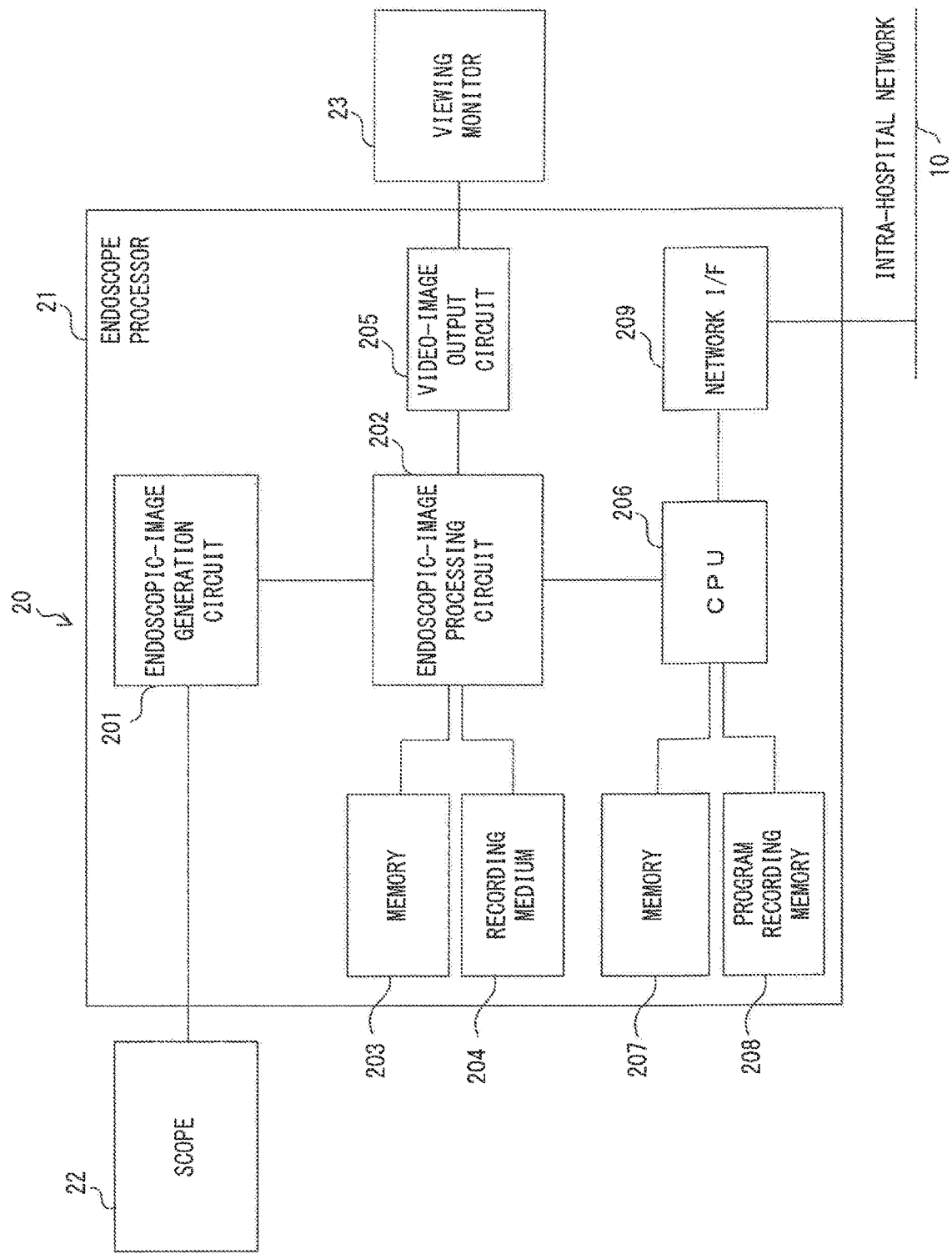
FIG. 2 illustrates an exemplary configuration of a video system center.

FIG. 2 illustrates an exemplary configuration of the video system center 20.

As depicted in FIG. 2, the video system center 20 includes an endoscope processor 21 connected to the intra-hospital network 10, a scope 22, and a viewing monitor 23, wherein the scope 22 and the viewing monitor 23 are connected to the endoscope processor 21.

A portion of the scope 22 is inserted into the body cavity of a subject (patient), an image capturing part provided at a leading-edge portion of the scope 22 captures an image of an examined site, and the scope 22 outputs an obtained image signal to the endoscope processor 21. The scope 22 includes an operation part to be operated by a user (e.g., a doctor).

The endoscope processor 21 includes an endoscopic-image generation circuit 201, an endoscopic-image processing circuit 202, a memory 203, a recording medium 204, a video-image output circuit 205, a central processing unit (CPU) 206, a memory 207, a program recording memory 208, and a network interface (I/F) 209.

The endoscopic-image generation circuit 201 generates an endoscopic image by applying predetermined signal processing to an image signal input from the scope 22.

The endoscopic-image processing circuit 202 applies predetermined image processing to an endoscopic image generated by the endoscopic-image generation circuit 201 and outputs the endoscopic image after the processing to the video-image output circuit 205. Under the control of the CPU 206, the endoscopic-image processing circuit 202 records the endoscopic image after the processing in the recording medium 204.

The video-image output circuit 205 generates an image by superimposing information such as characters onto the endoscopic image processed by the endoscopic-image processing circuit 202 and outputs the generated image to the viewing monitor 23.

The memory 203 is used as a work area for the endoscopic-image processing circuit 202 and has temporarily stored therein an endoscopic image in processing by the endoscopic-image processing circuit 202.

An endoscopic image processed by the endoscopic-image processing circuit 202 is recorded in the recording medium 204. Endoscopic images recorded in the recording medium 204 are still images and moving images, and those images are recorded in the recording medium 204 as image files (still image files and moving image files).

By reading and executing a program loaded from the program recording memory 208 into the memory 207, the CPU 206 executes an endoscopic examination process so as to control operations of the endoscope processor 21. The endoscopic examination process will be described hereinafter by referring to, for example, FIGS. 4-6. The CPU 206 also detects an operational state of the operation part of the scope 22.

The memory 207 is used as a memory into which a program recorded in the program recording memory 208 is loaded and as a work area for the CPU 206, and a program or data is temporarily stored in the memory 207.

The program recording memory 208 has stored therein a program to be executed by the CPU 206 and data to be used during execution of the program.

The network I/F 209 is connected to the intra-hospital network 10 and communicates with an external apparatus such as the endoscopic information management system 30 over the intra-hospital network 10.

The viewing monitor 23 displays, as a live video image, an image input from the video-image output circuit 205 of the endoscope processor 21.

Figure 3:
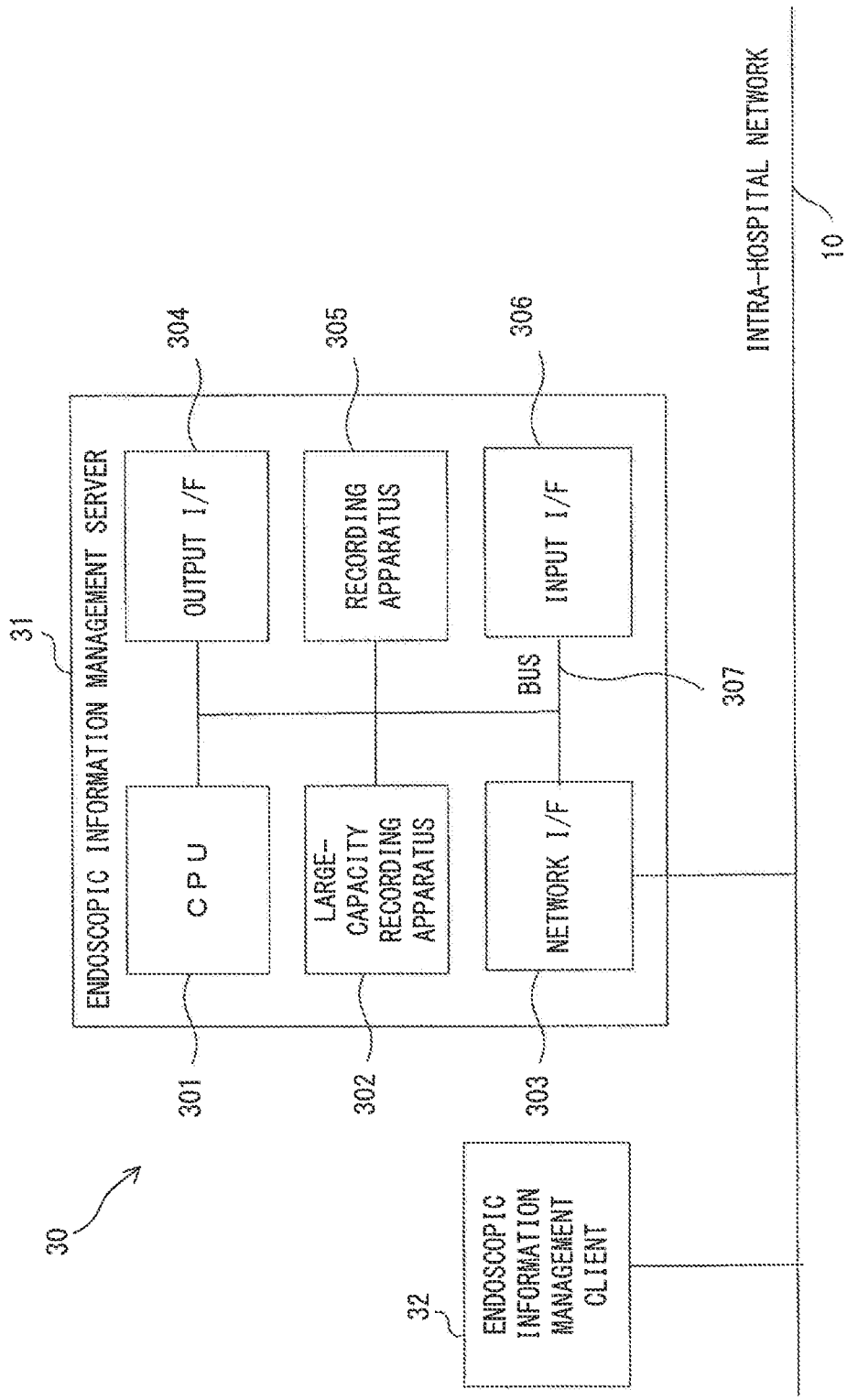
FIG. 3 illustrates an exemplary configuration of an endoscopic information management system.

FIG. 3 illustrates an exemplary configuration of the endoscopic information management system 30.

As depicted in FIG. 3, the endoscopic information management system 30 includes an endoscopic information management server 31 and an endoscopic information management client 32, both of which are connected to the intra-hospital network 10.

The endoscopic information management server 31 includes a CPU 301, a large-capacity recording apparatus 302, a network I/F 303, an output I/F 304, a recording apparatus 305, an input I/F 306, and a bus 307 connecting these components.

By reading and executing a program recorded in the recording apparatus 305, the CPU 301 executes an endoscopic examination process so as to control operations of the endoscopic information management server 31. The endoscopic examination process will be described hereinafter by referring to, for example, FIGS. 4-6.

The recording apparatus 305 is a memory, e.g., a random access memory (RAM) or a read only memory (ROM), and has stored therein a program to be executed by the CPU 301 and data to be used during execution of the program.

The large-capacity recording apparatus 302 is, for example, a hard disk and has recorded therein information related to an endoscopic examination that is managed by the endoscopic information management system 30 (e.g., endoscopic images).

The network I/F 303 is connected to the intra-hospital network 10 and communicates with external apparatuses such as the endoscopic information management client 32 and the video system center 20 over the intra-hospital network 10.

The output I/F 304 is an interface for establishing connections to output apparatuses such as a display, a printer, and a speaker.

The input I/F 306 is an interface for establishing connections to input apparatuses such as a keyboard, a mouse, a touch panel, a microphone, and a scanner.

The bus 307 is a transmission path through which data is transmitted or received between the apparatuses connected to the bus 307.

The endoscopic information management client 32 is, for example, a personal computer (PC) and, as with the video system center 20, provided within the endoscopic examination room. Although not illustrated, the endoscopic information management client 32 includes a CPU, a network I/F connected to the intra-hospital network 10, an output I/F to which a display has been connected, a recording apparatus, an input I/F to which a keyboard has been connected, and a bus connecting these components. The endoscopic information management client 32 communicates with an external apparatus such as the endoscopic information management server 31 over the intra-hospital network 10.

In the medical system 1 having such a configuration, the endoscope processor 21 is an example of the processor or the external processor. The endoscopic information management server 31 is an example of the management apparatus, the external management apparatus, or the endoscopic information management apparatus.

In the endoscope processor 21, some functions of the network I/F 209 correspond to an exemplary input unit to which reserved-examination identification information for identifying a preset reserved examination is input from an external management apparatus. Some functions of the CPU 206 correspond to an exemplary performed-examination identification information generation unit that generates first-performed-examination identification information for identifying a first performed examination performed as an examination based on the reserved examination and generates second-performed-examination identification information for identifying a second performed examination performed as an examination based on the reserved examination after the first performed examination is performed. Other functions of the CPU 206 correspond to an exemplary correlation unit that correlates the reserved-examination identification information and the first-performed-examination identification information with each other and correlates the reserved-examination identification information and the second-performed-examination identification information with each other. Other functions of the network I/F 209 correspond to an exemplary output unit that outputs the reserved-examination identification information and the first-performed-examination identification information correlated with each other and outputs the reserved-examination identification information and the second-performed-examination identification information correlated with each other.

In the endoscopic information management server 31, some functions of the network I/F 303 correspond to an exemplary output unit that outputs reserved-examination identification information for identifying a present reserved examination. Other functions of the network I/F 303 correspond to an exemplary input unit to which the reserved-examination identification information and first-performed-examination identification information that have been correlated with each other and the reserved-examination identification information and second-performed-examination identification information that have been correlated with each other are input from an external processor. Some functions of the CPU 301 correspond to an exemplary calculation unit that calculates the total number of pieces of data correlated with the reserved-examination identification information.

The following describes endoscopic examination processes performed by the medical system 1 in accordance with the present embodiment.

Figure 4A:
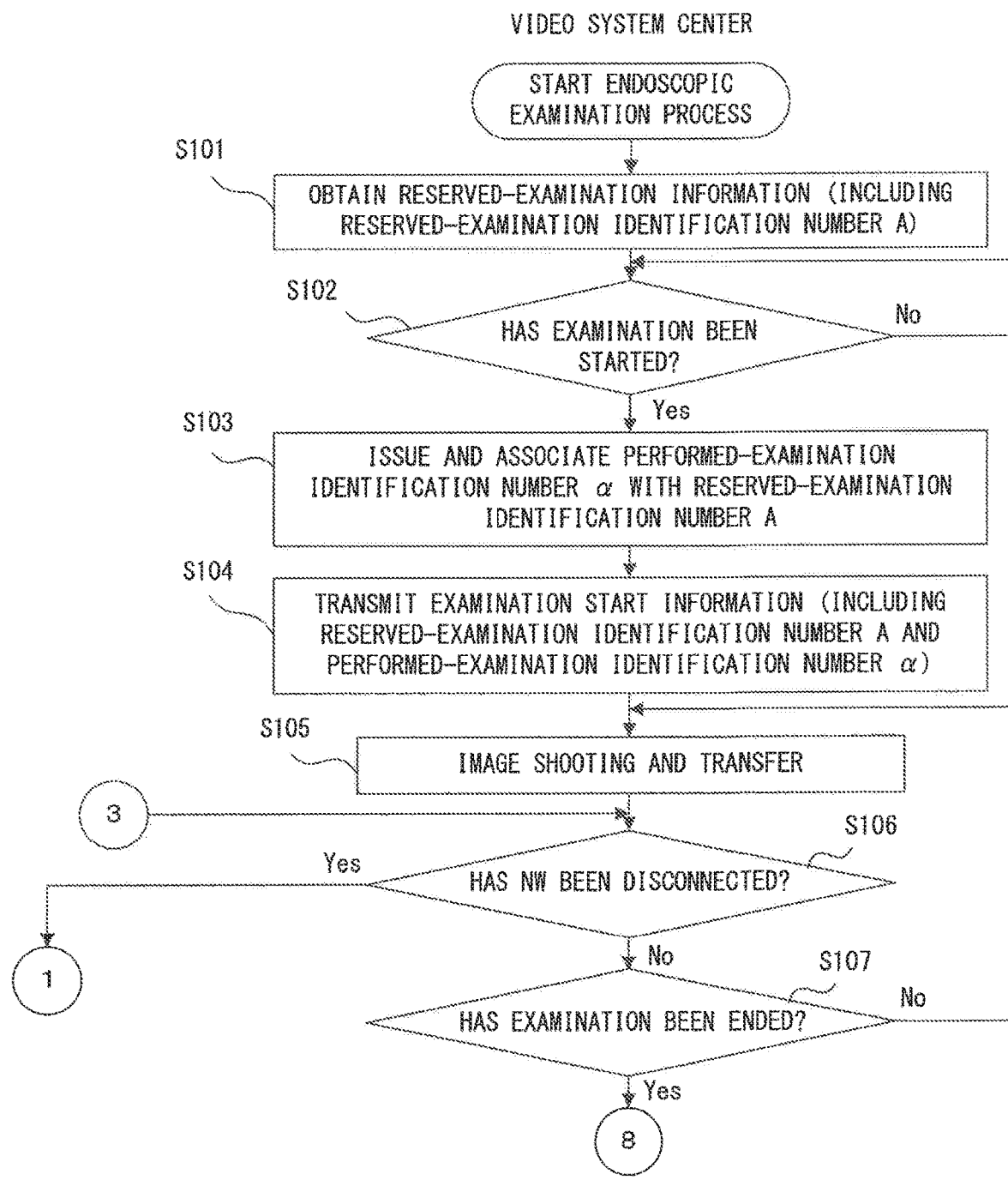
FIG. 4A is a flowchart illustrating an exemplary process performed by a video system center among endoscopic examination processes performed by a medical system (example 1)
Figure 4B:
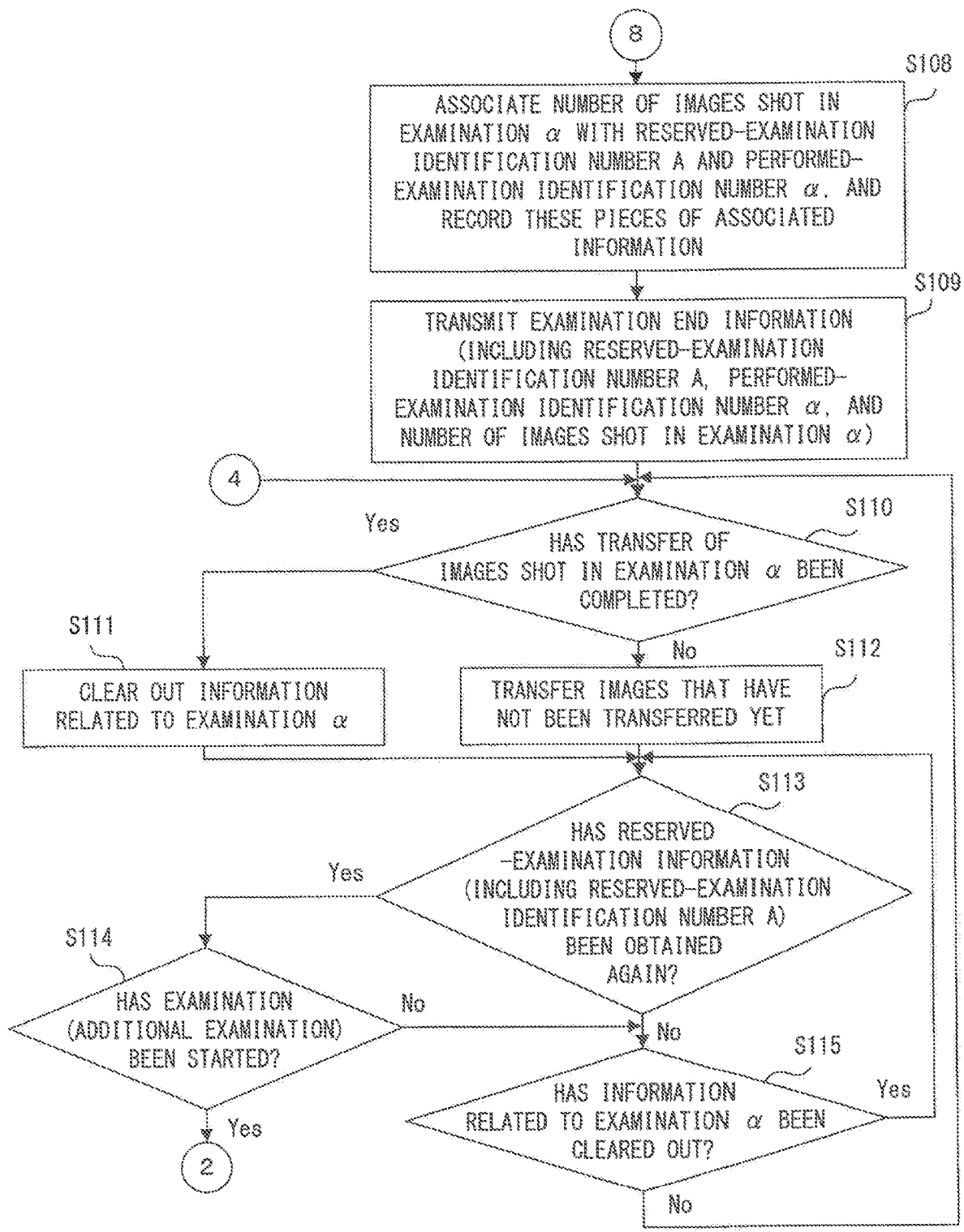
FIG. 4B is a flowchart illustrating an exemplary process performed by a video system center among endoscopic examination processes performed by a medical system (example 2)
Figure 5:
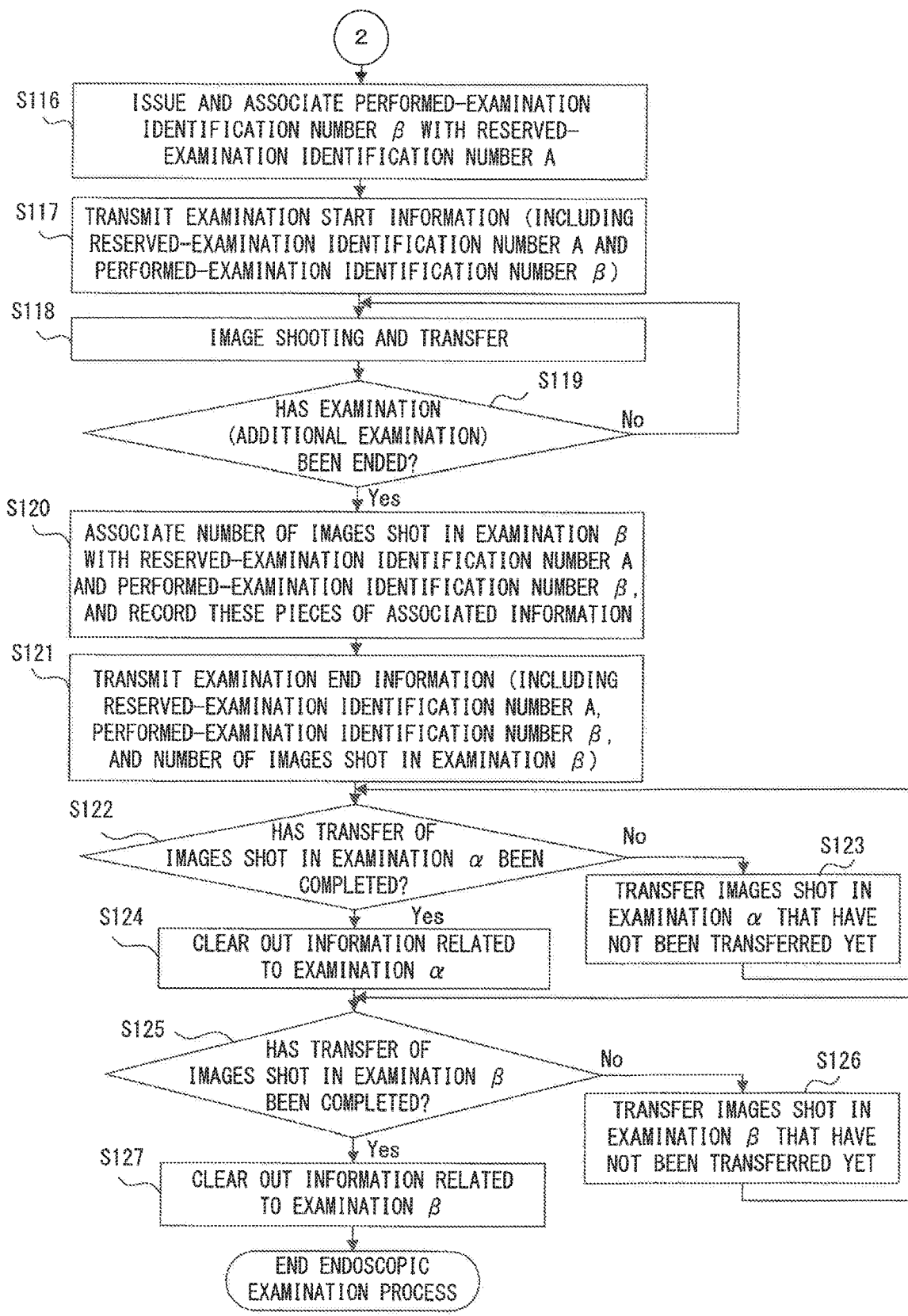
FIG. 5 is a flowchart illustrating an exemplary process performed by a video system center among endoscopic examination processes performed by a medical system (example 3)
Figure 6:
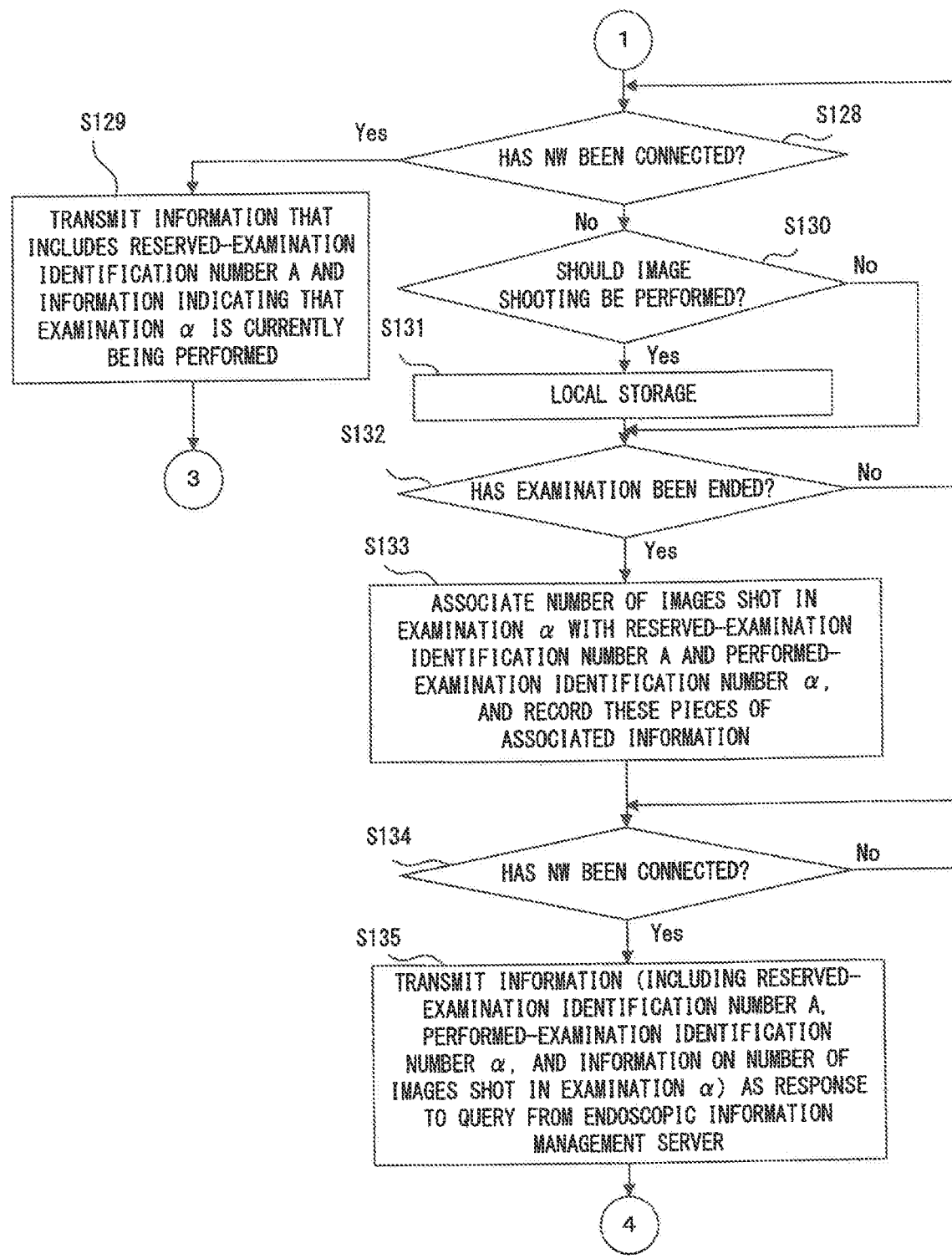
FIG. 6 is a flowchart illustrating an exemplary process performed by a video system center among endoscopic examination processes performed by a medical system (example 4)
Figure 7A:
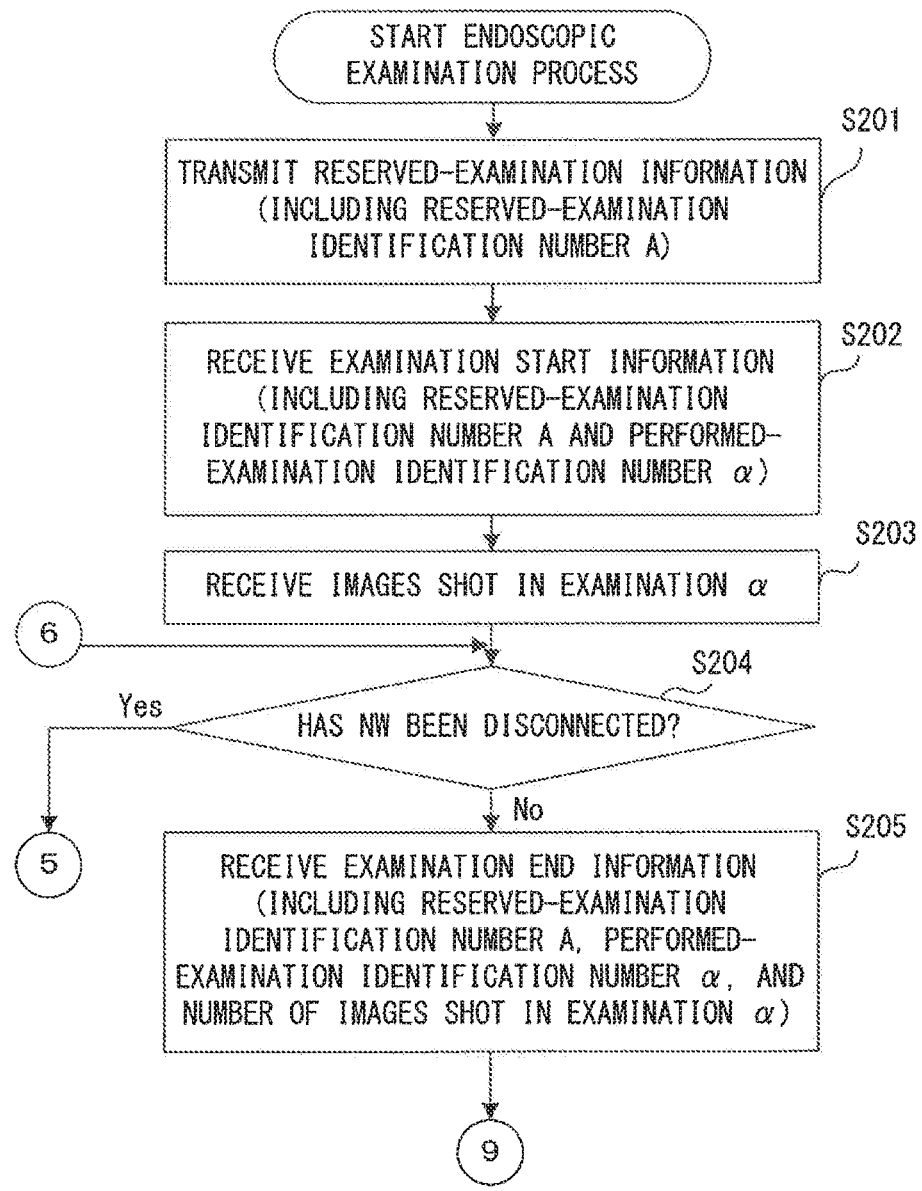
FIG. 7A is a flowchart illustrating an exemplary process performed by an endoscopic information management system among endoscopic examination processes performed by a medical system (example 1)
Figure 7B:
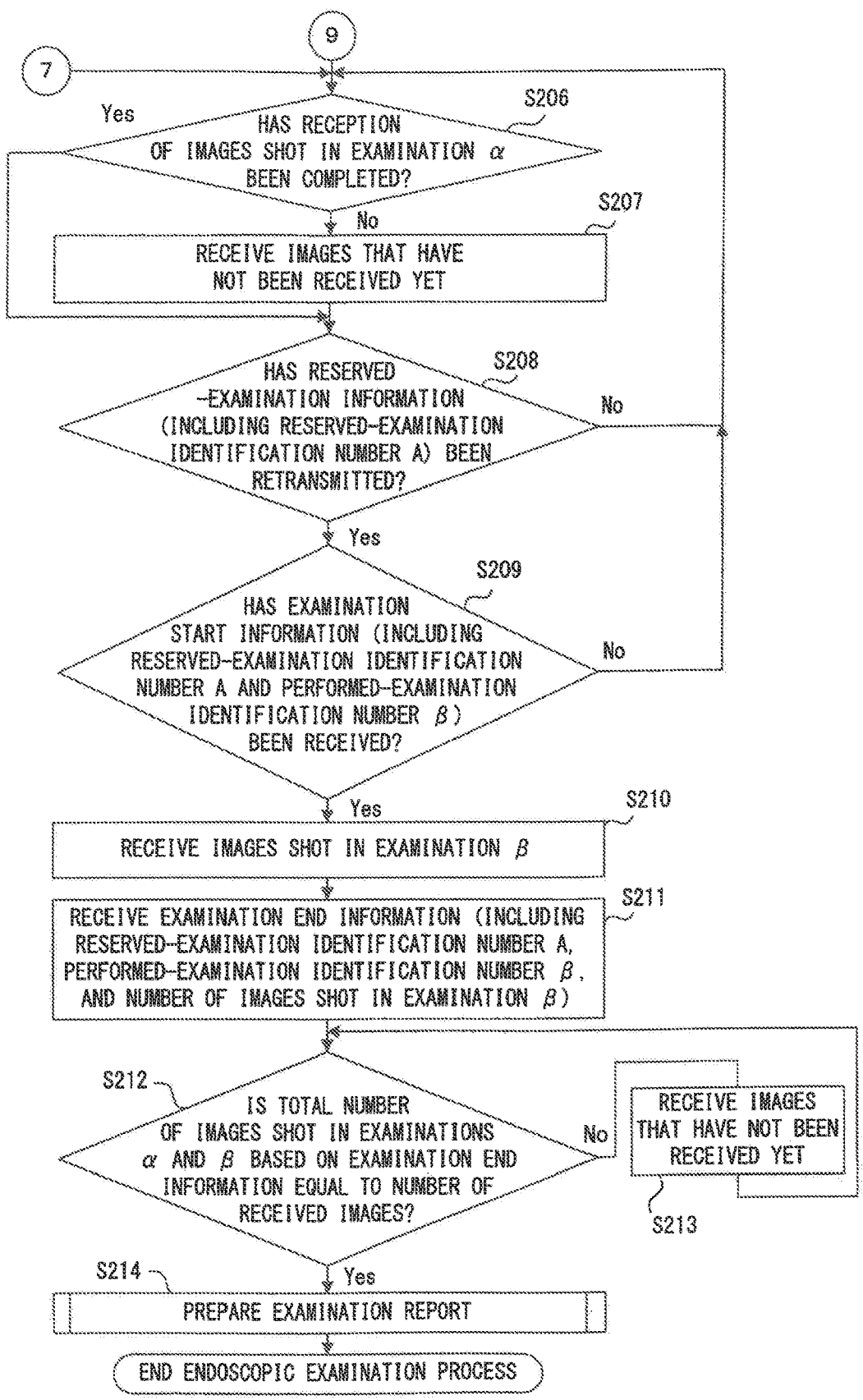
FIG. 7B is a flowchart illustrating an exemplary process performed by an endoscopic information management system among endoscopic examination processes performed by a medical system (example 2)
Figure 8:
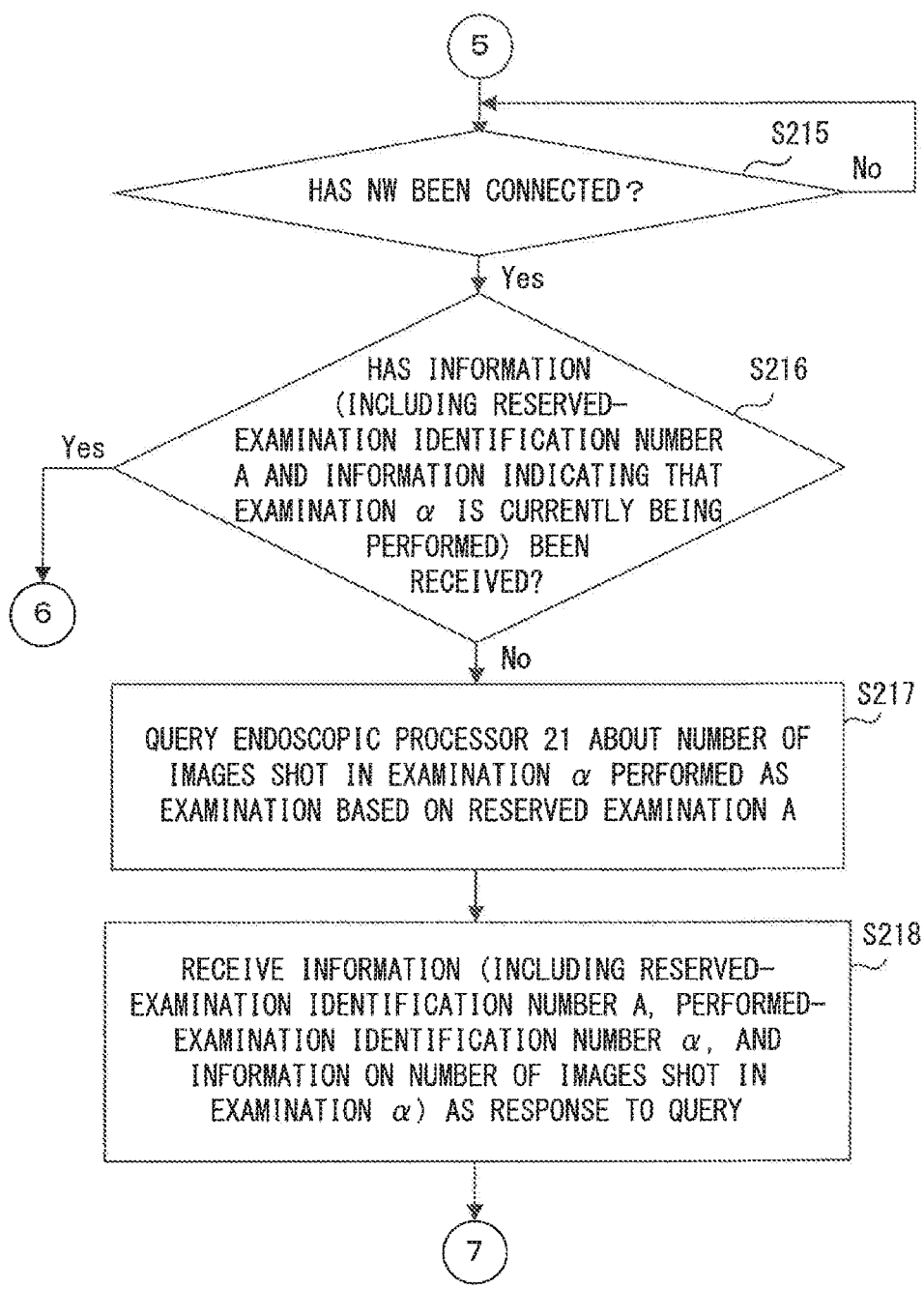
FIG. 8 is a flowchart illustrating an exemplary process performed by an endoscopic information management system among endoscopic examination processes performed by a medical system (example 3)

FIGS. 4-8 are flowcharts illustrating examples of the endoscopic examination processes. More particularly, FIGS. 4-6 are each a flowchart illustrating an exemplary process performed by the video system center 20 among the endoscopic examination processes. FIGS. 7 and 8 are each a flowchart illustrating an exemplary process performed by the endoscopic information management system 30 among the endoscopic examination processes. As endoscopic examination processes performed by the medical system 1, processes performed by the video system center 20 will first be described by referring to FIGS. 4-6, and processes performed by the endoscopic information management system 30 will then be described by referring to FIGS. 7 and 8. The following descriptions will be given on the assumption that endoscopic images obtained (shot) by the video system center 20 are still images, but these images, of course, may be moving images.

In the process performed by the video system center 20, first, the CPU 206 of the endoscope processor 21 obtains reserved examination information transmitted from the endoscopic information management server 31 in S201 in FIG. 7A (this will be described hereinafter) via the intra-hospital network 10 and the network I/F 209 (S101), as depicted in FIG. 4A. Reserved examination information is information related to a reserved examination preset by the endoscopic information management system 30 and includes a reserved-examination identification number for identifying the reserved examination (an example of the reserved-examination identification information). A reserved-examination identification number includes respective numbers representing a patient ID, an examination time-and-date, and an examined site (examples of the patient information, the examination time-and-date information, and the examined site information). For the sake of description, let "A" be the reserved-examination identification number included in the reserved examination information received in S101 in the present embodiment.

The CPU 206 determines whether an examination based on the reserved examination with the reserved-examination identification number "A" has been started (S102). The determination as to whether the examination has been started is made by, for example, the CPU 206 detecting whether a predetermined button included in the operation part of the scope 22 has been operated.

When the determination result of S102 is No, the determination of S102 is repeated.

When the determination result of S102 is Yes, the CPU 206 issues (generates) an examination identification number (performed-examination identification number) for identifying the examination started in S102 and associates (correlates) the performed-examination identification number with the reserved-examination identification number "A" (S103). For the sake of description, let "α" be the performed-examination identification number issued in S103 in the present embodiment. Accordingly, the examination started in S102 may be considered to be an examination with a reserved-examination identification number of "A" and a performed-examination identification number of "α". The performed-examination identification number is an example of the performed-examination identification information, the examination started in S102 is an example of the first performed examination, and the performed-examination identification number "α" is an example of the first-examined-examination identification information.

The CPU 206 transmits examination start information that includes the reserved-examination identification number "A" and the performed-examination identification number "α" associated with each other in S103 to the endoscopic information management server 31 via the network I/F 209 and the intra-hospital network 10 (S104).

The CPU 206 shoots and transfers endoscopic images (S105). More particularly, upon detection of the operating of a release button included in the operation part of the scope 22, the CPU 206 records, in the recording medium 204, endoscopic images shot by the scope 22, generated by the endoscopic-image generation circuit 201, and processed by the endoscopic-image processing circuit 202. The CPU 206 also transfers the endoscopic images to the endoscopic information management server 31 via the network I/F 209 and the intra-hospital network 10. The transferred endoscopic images are accompanied by the reserved-examination identification number "A" and the performed-examination identification number "α" so that it can be determined at a later time in which examination the endoscopic images were shot.

The CPU 206 determines whether the intra-hospital network 10 (NW) between the endoscope processor 21 and the endoscopic information management server 31 has been disconnected (S106). This determination is made by, for example, the CPU 206 determining whether the CPU 206 can communicate with the endoscopic information management server 31 via the network I/F 209 and the intra-hospital network 10.

When the determination result of S106 is No, the CPU 206 determines whether the examination started in S102 (the examination with the performed-examination identification number "α") has been ended (S107). The determination as to whether the examination has been ended is made by, for example, the CPU 206 detecting whether a predetermined button included in the operation part of the scope 22 has been operated.

When the determination result of S107 is No, the process returns to S105.

When the determination result of S107 is Yes, the CPU 206 associates, as depicted in FIG. 4B, information on the number of endoscopic images shot in S105 during the period extending from the start of the examination in S102 to the end of the examination in S107 (shot in the examination with the performed-examination identification number "α") with the reserved-examination identification number "A" and the performed-examination identification number "α" associated with each other in S103 and records these associated information and numbers in the memory 207 (S108). The number of the endoscopic images is also the number of image files of the endoscopic images.

The CPU 206 transmits examination end information to the endoscopic information management server 31 via the network I/F 209 and the intra-hospital network 10, the examination end information including the information and numbers associated and recorded in S108, i.e., the reserved-examination identification number "A", the performed-examination identification number "α", and the information on the number of endoscopic images shot in the examination with the performed-examination identification number "α" (S109).

The CPU 206 determines whether the transfer of the endoscopic images shot in the examination with the performed-examination identification number "α" to the endoscopic information management server 31 has been completed (S110).

When the determination result of S110 is Yes, the CPU 206 clears out the information related to the examination with the performed-examination identification number "α" that has been recorded in the memory 207 (S111). The information related to the examination with the performed-examination identification number "α" includes the information and numbers associated and recorded in S108, i.e., the reserved-examination identification number "A", the performed-examination identification number "α", and the information on the number of endoscopic images shot in the examination with the performed-examination identification number "α".

When the determination result of S110 is No, the CPU 206 transfers endoscopic images for which the transfer has not been completed (S112). The transferred endoscopic images are accompanied by the reserved-examination identification number "A" and the performed-examination identification number "α".

After S111 or S112, the CPU 206 determines again whether reserved-examination information that includes the reserved-examination identification number "A" has been obtained from the endoscopic information management server 31 via the intra-hospital network 10 and the network I/F 209 (S113).

Obtaining reserved-examination information that includes the reserved-examination identification number "A" from the endoscopic information management server 31 again means, for example, that after an examination with the performed-examination identification number "α" was performed as an examination based on the reserved examination with the reserved-examination identification number "A", a doctor has determined that an additional examination (e.g., the shooting of additional endoscopic images) needs to be performed as an examination based on the reserved examination with the reserved-examination identification number "A". In this situation, using the endoscopic information management client 32 provided within the endoscopic examination room, the doctor requests that the endoscopic information management server 31 retransmit reserved-examination information that includes the reserved-examination identification number "A", and in response to this, the reserved-examination information that includes the reserved-examination identification number "A" is retransmitted from the endoscopic information management server 31 to the video system center 20.

When the determination result of S113 is Yes, the CPU 206 determines whether an examination (additional examination) based on the reserved examination with the reserved-examination identification number "A" has been started (S114).

When the determination result of S113 is No, or when the determination result of S114 is No, the CPU 206 determines whether the information related to the examination with the performed-examination identification number "α" has been cleared out from the memory 207 (S115).

When the determination result of S115 is Yes, the process returns to S113, and when the determination result of S115 is No, the process returns to S110.

When the determination result of S114 is Yes, as depicted in FIG. 5, the CPU 206 issues (generates) an examination identification number (performed-examination identification number) for identifying the examination (additional examination) started in S114 and associates (correlates) the performed-examination identification number and the reserved-examination identification number "A" with each other (S116). In the present embodiment, for the sake of description, let "β" be the performed-examination identification number issued in S116. Accordingly, the examination started in S114 may be considered to be an examination with a reserved-examination identification number of "A" and a performed-examination identification number of "β". The examination started in S114 is an example of the second performed examination, and the performed-examination identification number "β" is an example of the second performed-examination identification information.

The CPU 206 transmits examination start information that includes the reserved-examination identification number "A" and the performed-examination identification number "β" associated with each other in S116 to the endoscopic information management server 31 via the network I/F 209 and the intra-hospital network 10 (S117).

As in S105, the CPU 206 shoots and transfers endoscopic images (S118). The transferred endoscopic images are accompanied by the reserved-examination identification number "A" and the performed-examination identification number "β".

The CPU 206 determines whether the examination started in S114 (the examination with the performed-examination identification number "β") has been ended (S119).

When the determination result of S119 is No, the process returns to S118.

When the determination result of S119 is Yes, the CPU 206 associates information on the number of endoscopic images shot in S118 during the period extending from the start of the examination in S114 to the end of the examination in S119 (shot in the examination with the performed-examination identification number "β") with the reserved-examination identification number "A" and the performed-examination identification number "β" associated with each other in S116 and records these associated information and numbers in the memory 207 (S120).

The CPU 206 transmits examination end information to the endoscopic information management server 31 via the network I/F 209 and the intra-hospital network 10, the examination end information including the information and numbers associated and recorded in S120, i.e., the reserved-examination identification number "A", the performed-examination identification number "β", and the information on the number of endoscopic images shot in the examination with the performed-examination identification number "β" (S121).

The CPU 206 determines whether the transfer of the endoscopic images shot in the examination with the performed-examination identification number "α" to the endoscopic information management server 31 has been completed (S122).

When the determination result of S122 is No, the CPU 206 transfers endoscopic images shot in the examination with the performed-examination identification number "α" for which the transfer has not been completed (S123), and the process returns to S122. The endoscopic images transferred in S123 are accompanied by the reserved-examination identification number "A" and the performed-examination identification number "α".

When the determination result of S122 is Yes, the CPU 206 clears out the information related to the examination with the performed-examination identification number "α" that has been recorded in the memory 207 (S124).

The CPU 206 determines whether the transfer of the endoscopic images shot in the examination with the performed-examination identification number "β" to the endoscopic information management server 31 has been completed (S125).

When the determination result of S125 is No, the CPU 206 transfers endoscopic images shot in the examination with the performed-examination identification number "β" for which the transfer has not been completed (S126), and the process returns to S125. The endoscopic images transferred in S126 are accompanied by the reserved-examination identification number "A" and the performed-examination identification number "β".

When the determination result of S125 is Yes, the CPU 206 clears out the information related to the examination with the performed-examination identification number "β" that has been recorded in the memory 207 (S127), and the process ends. The information related to the examination with the performed-examination identification number "β" includes the information and numbers associated and recorded in S120, i.e., the reserved-examination identification number "A", the performed-examination identification number "β", and the information on the number of endoscopic images shot in the examination with the performed-examination identification number "β".

When the determination result of S106 in FIG. 4A is Yes, as depicted in FIG. 6, the CPU 206 determines whether the intra-hospital network 10 (NW) between the endoscope processor 21 and the endoscopic information management server 31 has been connected (S128). This determination is made by, for example, the CPU 206 determining whether the CPU 206 can communicate with the endoscopic information management server 31 via the network I/F 209 and the intra-hospital network 10, as in S106 in FIG. 4A.

When the determination result of S128 is Yes, the CPU 206 transmits information that includes the reserved-examination identification number "A" and information indicating that the examination with the performed-examination identification number "α" is currently being performed to the endoscopic information management server 31 via the network I/F 209 and the intra-hospital network 10 (S129), and the process returns to S106 in FIG. 4A.

When the determination result of S128 is No, the CPU 206 determines whether an image shooting instruction for endoscopic images has been given (S130). This determination is made by, for example, the CPU 206 detecting whether a release button included in the operation part of the scope 22 has been operated.

When the determination result of S130 is Yes, the CPU 206 records, in the recording medium 204 (local storage), endoscopic images shot by the scope 22, generated by the endoscopic-image generation circuit 201, and processed by the endoscopic-image processing circuit 202 (S131).

When the determination result of S130 is No, or after S131 is performed, the CPU 206 determines whether the examination started in S102 in FIG. 4A (the examination with the performed-examination identification number "α") has been ended (S132).

When the determination result of S132 is No, the process returns to S128.

When the determination result of S132 is Yes, the CPU 206 associates information on the total number of endoscopic images shot in S105 during the period extending from the start of the examination in S102 to the end of the examination in S132 (shot in the examination with the performed-examination identification number "α") and endoscopic images shot in accordance with the image shooting instruction in S130 during that period with the reserved-examination identification number "A" and the performed-examination identification number "α" associated with each other in S103 in FIG. 4A and records these associated information and numbers in the memory 207 (S133).

The CPU 206 determines whether the intra-hospital network 10 (NW) between the endoscope processor 21 and the endoscopic information management server 31 has been connected (S134).

When the determination result of S134 is No, the determination of S134 is repeated.

When the determination result of S134 is Yes, the CPU 206 transmits, as a response to a query from the endoscopic information management server 31 that is made in S217 in FIG. 8 (this will be described hereinafter), information that includes the information and numbers associated and recorded in S133, i.e., the reserved-examination identification number "A", the performed-examination identification number "α", and the information on the number of endoscopic images shot in the examination with the performed-examination identification number "α", to the endoscopic information management server 31 via the network I/F 209 and the intra-hospital network 10 (S135), and the process shifts to S110 in FIG. 4B. The query from the endoscopic information management server 31 is one about the number of endoscopic images shot in the examination with the performed-examination identification number "α" performed as an examination based on the reserved examination with the reserved-examination identification number "A".

In the process performed by the endoscopic information management system 30, first, the CPU 301 of the endoscopic information management server 31 transmits, as depicted in FIG. 7A, reserved-examination information that includes the reserved-examination identification number "A" to the endoscope processor 21 via the network I/F 303 and the intra-hospital network 10 (S201). As described above, the reserved-examination information that includes the reserved-examination identification number "A" is information related to a reserved examination with the reserved-examination identification number "A" that is preset by the endoscopic information management system 30.

The CPU 301 receives the examination start information transmitted from the endoscope processor 21 in S104 in FIG. 4A described above (including the reserved-examination identification number "A" and the performed-examination identification number "α") via the intra-hospital network 10 and the network I/F 303 (S202).

The CPU 301 receives the endoscopic images transferred from the endoscope processor 21 in S105 in FIG. 4A described above via the intra-hospital network 10 and the network I/F 303 (S203). The received endoscopic images are recorded in the large-capacity recording apparatus 302.

The CPU 301 determines whether the intra-hospital network 10 (NW) between the endoscopic information management server 31 and the endoscope processor 21 has been disconnected (S204). This determination is made by, for example, the CPU 301 determining whether the CPU 301 can communicate with the endoscope processor 21 via the network I/F 303 and the intra-hospital network 10.

When the determination result of S204 is No, the CPU 301 receives the examination end information transmitted from the endoscope processor 21 in S109 in FIG. 4B described above (including the reserved-examination identification number "A", the performed-examination identification number "α", and the information on the number of endoscopic images shot in the examination with the performed-examination identification number "α") via the intra-hospital network 10 and the network I/F 303 (S205).

As depicted in FIG. 7B, the CPU 301 determines whether the reception of the endoscopic images shot in the examination with the performed-examination identification number "α" has been completed (S206). This determination is made on the basis of, for example, whether the number of the endoscopic images received in S203 is equal to the number of endoscopic images obtained from the examination end information received in S205 or from information obtained in S218 in FIG. 8 (this will be described hereinafter).

When the determination result of S206 is No, the CPU 301 receives endoscopic images shot in the examination with the performed-examination identification number "α" for which the reception has not been completed (S207). The received endoscopic images are recorded in the large-capacity recording apparatus 302.

When the determination result of S206 is Yes, or after S207 is performed, the CPU 301 determines whether the reserved-examination information that includes the reserved-examination identification number "A" has been retransmitted (S208). As described above, the retransmitting is performed in response to, for example, the doctor requesting that the endoscopic information management server 31 retransmit the reserved-examination information that includes the reserved-examination identification number "A", by using the endoscopic information management client 32 provided within the endoscopic examination room.

When the determination result of S208 is No, the process returns to S206.

When the determination result of S208 is Yes, the CPU 301 determines whether the examination start information transmitted from the endoscope processor 21 in S117 in FIG. 5 described above (including the reserved-examination identification number "A" and the performed-examination identification number "β") has been received via the intra-hospital network 10 and the network I/F 303 (S209).

When the determination result of S209 is No, the process returns to S206.

When the determination result of S209 is Yes, the CPU 301 receives the endoscopic images transferred from the endoscope processor 21 in S118 in FIG. 5 described above via the intra-hospital network 10 and the network I/F 303 (S210). The received endoscopic images are recorded in the large-capacity recording apparatus 302.

The CPU 301 receives the examination end information transmitted from the endoscope processor 21 in S121 in FIG. 5 described above (including the reserved-examination identification number "A", the performed-examination identification number "β", and the information on the number of endoscopic images shot in the examination with the performed-examination identification number "β") via the intra-hospital network 10 and the network I/F 303 (S211).

The CPU 301 totalizes the number of endoscopic images obtained from the examination end information received in S205 or from information received in S218 in FIG. 8 (this will be described hereinafter) (the number of endoscopic images shot in the examination with the performed-examination identification number "α") and the number of endoscopic images obtained from the examination end information received in S211 (the number of endoscopic images shot in the examination with the performed-examination identification number "β"), and determines whether the total number is equal to the total number of endoscopic images received in S203, S207, and S210 (S212).

When the determination result of S212 is No, the CPU 301 receives endoscopic images for which the reception has not been completed (endoscopic images shot in either of or both of the respective examinations with the performed-examination identification numbers "α" and "β") (S213), and the process returns to S212. The endoscopic images received in S213 are recorded in the large-capacity recording apparatus 302.

When the determination result of S212 is Yes, the CPU 301 prepares an examination report (including information on examination results) related to the examinations performed as examinations based on the reserved examination with the reserved-examination identification number "A" (the respective examinations with the performed-examination identification numbers "α" and "β") (S214), and the process ends. The examination report prepared in S214 is recorded in the large-capacity recording apparatus 302. As described above, the endoscopic information management server 31 manages the examination results related to the reserved examination with the reserved-examination identification number "A" on the basis of the reserved-examination identification number "A" and the performed-examination identification number "α" correlated with each other and the reserved-examination identification number "A" and the performed-examination identification number "β" correlated with each other.

When the determination result of S204 is Yes, the CPU 301 determines, as depicted in FIG. 8, whether the intra-hospital network 10 (NW) between the endoscopic information management server 31 and the endoscope processor 21 has been connected (S215). This determination is made by, for example, the CPU 301 determining whether the CPU 301 can communicate with the endoscope processor 21 via the network I/F 303 and the intra-hospital network 10, as in S204 in FIG. 7A.

When the determination result of S215 is No, the determination of S215 is repeated.

When the determination result of S215 is Yes, the CPU 301 determines whether the information transmitted from the endoscope processor 21 in S129 in FIG. 6 described above (including the reserved-examination identification number "A" and the information indicating that the examination with the performed-examination identification number "α" is currently being performed) has been received via the intra-hospital network 10 and the network I/F 303 (S216).

When the determination result of S216 is Yes, the process returns to S204 in FIG. 7A.

When the determination result of S216 is No, the CPU 301 queries the endoscope processor 21 about the number of endoscopic images shot in the examination with the performed-examination identification number "α" performed as an examination based on the reserved examination with the reserved-examination identification number "A" (S217).

The CPU 301 receives, as a response to the query made in S217, the information transmitted from the endoscope processor in S135 in FIG. 6 described above (including the reserved-examination identification number "A", the performed-examination identification number "α", and the information on the number of endoscopic images shot in the examination with the performed-examination identification number "α") (S218), and the process returns to S206 in FIG. 7B.

In the endoscopic examination process described using FIGS. 4-8, a performed-examination identification number is issued for each examination performed as an examination based on a reserved examination (see S103 in FIG. 4A and S116 in FIG. 5). When each individual examination is ended, examination end information that includes a reserved-examination identification number, the performed-examination identification number of the examination, and information on the number of endoscopic images shot in the examination is transmitted from the video system center 20 to the endoscopic information management system 30 (see S109 in FIG. 4B and S121 in FIG. 5). Accordingly, by totalizing the number of endoscopic images obtained from examination end information transmitted when each individual examination is ended, the endoscopic information management system 30 can figure out the total number of endoscopic images shot in examinations performed as examinations based on the reserved examination (see S212 in FIG. 7B).

In a case where during an examination, the intra-hospital network 10 between the video system center 20 and the endoscopic information management system 30 is disconnected and then the intra-hospital network 10 is connected, examination end information may not be transmitted. In this case, however, at the moment at which the intra-hospital network 10 is connected, the endoscopic information management system 30 queries the video system center 20 about the number of endoscopic images shot in the examination, so that the endoscopic information management system 30 can figure out the number of endoscopic images (S135 in FIG. 6 and S217 and S218 in FIG. 8).

In a case where during an examination, the intra-hospital network 10 between the video system center 20 and the endoscopic information management system 30 is disconnected and then the intra-hospital network 10 is connected, the information related to the examination is not cleared out in the video system center 20 until the transfer of the endoscopic images shot in the examination to the endoscopic information management system 30 is completed (see S110 and S111 in FIG. 4B). This also means that when the intra-hospital network 10 connected to the endoscopic information management system 30 is disconnected during an examination, the information related to the examination is not cleared out until the intra-hospital network 10 is connected.

As described above, in the medical system 1 in accordance with the present embodiment, even when an examination based on a reserved examination is performed and then an additional examination is performed as an examination based on the reserved examination, or even when the intra-hospital network 10 is disconnected and connected during an examination, the total number of endoscopic images shot in the examinations performed as examinations based on the reserved examination can be figured out.

The following modifications may be made to the medical system 1.

For example, in preparation for a situation in which an examination is restarted after being interrupted to exchange the scope 22, the endoscopic examination process depicted in FIGS. 4-8 may be changed in a manner such that the total number of endoscopic images shot in the examination before the interruption and after the restart can be figured out. In this case, for example, the endoscopic examination process depicted in FIGS. 4-8 may be changed to treat the examination before the interruption as an examination with a performed-examination identification number "α" and to treat the examination after the restart as an examination with a performed-examination identification number "β". More particularly, for example, a change may be made to provide a new step in which when the determination result of S106 in FIG. 4A is No, a determination is made as to whether the scope 22 has been exchanged, wherein when the determination result is Yes, the process shifts to S108 on the basis of the determination that the examination has been ended, and when the determination result is No, the process shifts to S107. A change is also made such that the reserved-examination information obtained again in S113 in FIG. 4B is reserved-examination information retransmitted from the endoscopic information management server 31 at the doctor's request to restart the examination.

For example, the medical system 1 may further perform the process described in the following as an endoscopic examination process. FIG. 9 is a flowchart illustrating an example of this process.

As depicted in FIG. 9A, in this process, the endoscopic information management server 31 (CPU 301) determines whether examination end information has been received from the endoscope processor 21 (S301). As described above, the examination end information includes a reserved-examination identification number, a performed-examination identification number, and information on the number of endoscopic images (endoscopic image count) shot in the examination with the performed-examination identification number.

When the determination result of S301 is Yes, the endoscopic information management server 31 determines whether the obtained endoscopic image count is equal to the number of received endoscopic images accompanied by the same performed-examination identification number (or the same reserved-examination identification number and the same performed-examination identification number) (S302).

When the determination result of S302 is No, the endoscopic information management server 31 receives endoscopic images shot in the examination from the endoscope processor 21 (S303), and the process returns to S302. The endoscopic images received in S303 are each accompanied by image identification information for identifying the endoscopic image, in addition to the reserved-examination identification number and the performed-examination identification number.

When the determination result of S302 is Yes, the endoscopic information management server 31 determines whether there are examinations with the same reserved-examination identification number that have an incomplete status (S304).

When the determination result of S304 is Yes, the process returns to S301.

When the determination result of S304 is No, the endoscopic information management server 31 determines whether there are a plurality of examinations with the same reserved-examination identification number (S305). A situation in which there are a plurality of examinations with the same reserved-examination identification number means that there are a plurality of examinations with the same reserved-examination identification number and different performed-examination identification numbers.

When the determination result of S305 is Yes, the endoscopic information management server 31 sums endoscopic image counts related to the plurality of examinations with the same reserved-examination identification number (S306).

When the determination result of S305 is No, or after S306 is performed, the process ends.

Figure 9B:
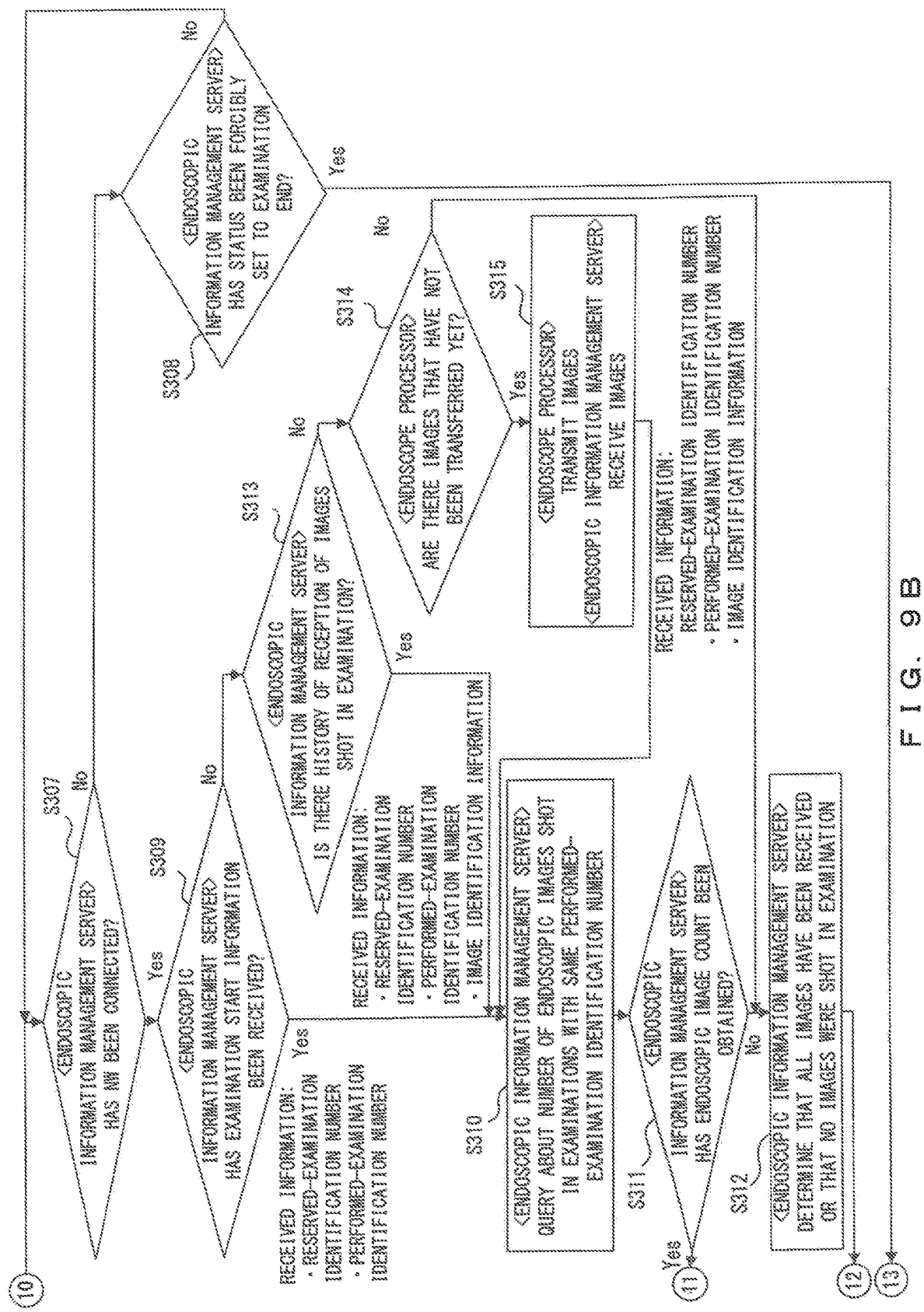
FIG. 9B is a flowchart illustrating an exemplary process further performed as an endoscopic examination process performed by a medical system (example 2).

When the determination result of S301 is No, the endoscopic information management server 31 determines, as depicted in FIG. 9B, whether the intra-hospital network 10 (NW) between the endoscopic information management server 31 and the endoscope processor 21 has been connected (S307).

When the determination result of S307 is No, the endoscopic information management server 31 determines whether the status has forcibly been set to examination end (S308). In the endoscopic information management server 31, when, for example, the endoscopic information management server 31 cannot communicate with the endoscope processor 21 for a predetermined time period or longer, the status is forcibly set to examination end.

When the determination result of S308 is No, the process returns to S307.

When the determination result of S308 is Yes, the process ends, as depicted in FIG. 9A.

When the determination result of S307 is Yes, the endoscopic information management server 31 determines whether examination start information has been received from the endoscope processor 21 (S309). As described above, examination start information includes information on a reserved-examination identification number and a performed-examination identification number.

When the determination result of S309 is Yes, the endoscopic information management server 31 queries the endoscope processor 21 about the number of endoscopic images (endoscopic image count) shot in examinations with the same performed-examination identification number (or in examinations with the same reserved-examination identification number and the same performed-examination identification number) (S310).

The endoscopic information management server 31 determines whether the endoscopic image count has been obtained from the endoscope processor 21 as a response to the query (S311).

When the determination result of S311 is Yes, the process shifts to S302 in FIG. 9A.

When the determination result of S311 is No, the endoscopic information management server 31 determines that all of the endoscopic images shot in the examination have been received or that no endoscopic images were shot in the examination (S312), and the process shifts to S304 in FIG. 9A.

When the determination result of S309 is No, the endoscopic information management server 31 determines whether there is a history of reception of endoscopic images shot in the examination (S313). The received endoscopic images are each accompanied by image identification information for identifying the endoscopic image, in addition to the reserved-examination identification number and the performed-examination identification number.

When the determination result of S313 is Yes, the process shifts to S310.

When the determination result of S313 is No, the endoscope processor 21 (CPU 206) determines whether there are endoscopic images shot in the examination that has not been transferred yet (S314).

When the determination result of S314 is Yes, the endoscope processor 21 transfers endoscopic images that have not been transferred yet, and the endoscopic information management server 31 receives the endoscopic images (315). Then, the process shifts to S310. The received endoscopic images are each accompanied by image identification information for identifying the endoscopic image, in addition to the reserved-examination identification number and the performed-examination identification number.

When the determination result of S314 is No, the process shifts to S312.

In the process depicted in FIG. 9, for example, the intra-hospital network 10 may be disconnected after examination start information is transmitted but before examination end information is transmitted, and after this, when the intra-hospital network 10 is connected (see the determination of Yes in S309), the number of endoscopic images shot in the examination may be queried about (see S310). When an endoscopic image count is not obtained as a response to the query (see the determination of No in S311), it is determined that all of the endoscopic images shot in the examination have been received or that no endoscopic images were shot in the examination (see S312), and endoscopic image counts are summed. Even in such a situation, accordingly, the total number of endoscopic images shot in examinations performed as examinations based on a reserved examination can be figured out.

The embodiments described above indicate specific examples of the present invention to facilitate understanding of the invention, and the present invention is not limited to those embodiments. Various modifications or changes can be made without departing from the spirit of the invention defined by the claims.

What is claimed is:

1. A medical system comprising:
a processor of an endoscope; and
a management apparatus, wherein:
the processor of the endoscope includes:
an input unit to which reserved-examination identification information for identifying a preset reserved examination is input from the management apparatus,
a performed-examination identification information generation unit that generates first-performed-examination identification information in correlation with the reserved-examination identification information and generates second-performed-examination identification information in correlation with the reserved-examination identification information, the first-performed-examination identification information identifying a first performed examination performed in response to the reserved-examination identification information input to the input unit, the second-performed-examination identification information identifying a second performed examination performed in response to the same reserved-examination identification information as the reserved-examination identification information input to the input unit,
a non-transitory recording medium that records a first-performed-examination result and a second-performed-examination result, the first-performed-examination result being data obtained by the endoscope in the first performed examination and accompanied by the first performed-examination identification information, the second-performed-examination result being data obtained by the endoscope in the second performed examination and accompanied by the second performed-examination identification information; and
a memory that records first count information and second count information, the first count information being related to a number of pieces of data obtained by the endoscope in the first performed examination and associated with the first-performed-examination identification information, the second count information being related to a number of pieces of data obtained by the endoscope in the second performed examination and associated with the second-performed-examination identification information,
the management apparatus includes:
a recording apparatus that records the first performed-examination result accompanied by the first-performed-examination identification information and the second performed-examination result accompanied by the second-performed-examination identification information, the first and second performed-examination results being transmitted from the recording medium of the processor of the endoscope, and
a calculation unit that calculates a total number of pieces of data of the first and second performed-examination results recorded in the recording apparatus that are accompanied by pieces of performed-examination identification information generated in correlation with same reserved-examination identification information, and
when a sum of the numbers indicated by the first and second count information transmitted from the memory of the processor of the endoscope that have been associated with pieces of performed-examination identification information generated in correlation with same reserved-examination identification information is not equal to the total number of pieces of data calculated by the calculation unit, the management apparatus receives data that has not been recorded in the recording apparatus of the management apparatus among the data recorded in the recording medium of the processor of the endoscope.

2. The medical system of claim 1, wherein
the first-performed-examination result is at least either still image data or moving image data, and
the first count information relates to at least either a number of still images or a number of moving image files.

3. The medical system of claim 1, wherein the reserved-examination identification information includes patient information, examination time-and-date information, and examined site information.

4. The medical system of claim 1, wherein the management apparatus manages the first and second performed-examination results recorded by the recording apparatus that are accompanied by pieces of performed-examination identification information generated in correlation with same reserved-examination identification information based on the performed-examination identification information.

5. The medical system of claim 1, wherein
the processor of the endoscope and the management apparatus are connected over a predetermined network,
when communication between the processor of the endoscope and the management apparatus over the predetermined network has been disconnected, after the predetermined network is reconnected, the processor of the endoscope transmits the first count information recorded by the memory that relates to the first performed examination performed before the predetermined network was disconnected, and
when a number of pieces of data recorded in the recording apparatus of the management apparatus by a time before the predetermined network was disconnected is not equal to the number indicated by the first count information transmitted from the memory after the predetermined network was reconnected, the management apparatus receives data that had not been recorded in the recording apparatus of the management apparatus by the time before the predetermined network was disconnected, among the data recorded in the recording medium of the processor of the endoscope.

6. The medical system of claim 1, wherein after a transfer of data that has not been recorded in the recording apparatus of the management apparatus has been completed, the processor of the endoscope deletes the data recorded in the memory of the processor of the endoscope.

7. The medical system of claim 1, wherein
the management apparatus is an endoscopic information management apparatus that is configured to be communicable with the processor of the endoscope and that manages information received from the processor of the endoscope.

8. A processor of an endoscope, the processor comprising:
an input unit to which reserved-examination identification information for identifying a preset reserved examination is input from an external management apparatus;
a performed-examination identification information generation unit that generates first-performed-examination identification information in correlation with the reserved-examination identification information and generates second-performed-examination identification information in correlation with the reserved-examination identification information, the first-performed-examination identification information identifying a first performed examination performed in response to the reserved-examination identification information input to the input unit, the second-performed-examination identification information identifying a second performed examination performed in response to the same reserved-examination identification information as the reserved-examination identification information input to the input unit;

a non-transitory recording medium that records a first-performed-examination result and a second-performed-examination result, the first-performed-examination result being data obtained by the endoscope in the first performed examination and accompanied by the first performed-examination identification information, the second-performed-examination result being data obtained by the endoscope in the second performed examination and accompanied by the second performed-examination identification information; and a memory that records first count information and second count information, the first count information being related to a number of pieces of data obtained by the endoscope in the first performed examination and associated with the first-performed-examination identification information, the second count information being related to a number of pieces of data obtained by the endoscope in the second performed examination and associated with the second-performed-examination identification information, wherein when a total number of pieces of data of the first and second performed-examination results transmitted from the recording medium, recorded in a recording apparatus within the external management apparatus, and accompanied by pieces of performed-examination identification information generated in correlation with same reserved-examination identification information, is not equal to a sum of the numbers indicated by the first and second count information transmitted from the memory to the external management apparatus and associated with pieces of performed-examination identification information generated in correlation with same reserved-examination identification information, the processor of the endoscope transmits data that has not been recorded in the recording apparatus of the external management apparatus, among the data recorded in the recording medium.

9. A management apparatus comprising:

a non-transitory recording apparatus that records first and second performed-examination results transmitted from an external processor of an endoscope, the first performed-examination result being data obtained by the endoscope in a first performed examination performed in response to reserved-examination identification information input to the external processor of the endoscope, the first performed-examination result being accompanied by first-performed-examination identification information generated in correlation with the reserved-examination identification information so as to identify the first performed examination, the second performed-examination result being data obtained by the endoscope in a second performed examination performed in response to the same reserved-examination identification information as the reserved-examination identification information input to the external processor of the endoscope, the second performed-examination result being accompanied by second-performed-examination identification information generated in correlation with the reserved-examination identification information so as to identify the second performed examination; and a calculation unit that calculates a total number of pieces of data of the first and second performed-examination results recorded by the recording apparatus and accompanied by pieces of performed-examination identification information generated in correlation with same reserved-examination identification information, wherein the management apparatus receives first count information and second count information from the external processor of the endoscope, the first count information being related to a number of pieces of data obtained in the first performed examination and associated with the first-performed-examination identification information, the second count information being related to a number of pieces of data obtained in the second performed examination and associated with the second-performed-examination identification information, and when a sum of the numbers indicated by the first and second count information associated with pieces of performed-examination identification information generated in correlation with same reserved-examination identification information is not equal to the total number of pieces of data calculated by the calculation unit, the management apparatus receives, from the external processor of the endoscope, data that has not been recorded in the recording apparatus.

* * * * *